(12) United States Patent
Page et al.

(10) Patent No.: US 12,064,272 B2
(45) Date of Patent: Aug. 20, 2024

(54) DETECTION OF PROSTATE CANCER (71) Applicant: Next Generation AI Pty Ltd, Highton (AU)

(72) Inventors: Mark Page, Highton (AU); Peter Brotchie, Highton (AU)

(73) Assignee: Next Generation AI Pty Ltd, Highton (AU)

( * ) Notice: Subject to any disclaimer, the term of this patent is extended or adjusted under 35 U.S.C. 154(b) by 0 days.

(21) Appl. No.: 18/133,256

(22) Filed: Apr. 11, 2023

(65) Prior Publication Data

US 2023/0320676 A1 Oct. 12, 2023

(30) Foreign Application Priority Data

Apr. 11, 2022 (AU) .................................. 2022202380

(51) Int. Cl.
*A61B 6/02* (2006.01)
*G06T 7/00* (2017.01)
*G06T 11/00* (2006.01)

(52) U.S. Cl.
CPC .............. *A61B 6/02* (2013.01); *G06T 7/0012* (2013.01); *G06T 11/008* (2013.01); *G06T 2207/10072* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 10,347,010 B2* | 7/2019 | Risman | G06V 10/774 |
| 11,116,995 B2* | 9/2021 | Khuntia | A61N 5/1031 |
| 2018/0033144 A1* | 2/2018 | Risman | G06T 7/0014 |
| 2018/0350066 A1* | 12/2018 | Zuyev | G06T 11/008 |
| 2020/0012761 A1* | 1/2020 | El-Baz | G16B 40/20 |

OTHER PUBLICATIONS

Chen, Liang, et al., "Self-Supervised Feature Learning for Medical Image Analysis", Med. Image Anal. https:// doi. org/ 10. 1016/j. media. 2019. 101539 (2019), (Jul. 24, 2018), 13 pgs.

(Continued)

*Primary Examiner* — Nancy Bitar
(74) *Attorney, Agent, or Firm* — Schwegman Lundberg & Woessner, P.A.

(57) ABSTRACT

This disclosure relates to detecting prostate cancer. A processor receives image data indicative of a computed tomography scan comprising a spatial sequence of two-dimensional cross-sectional images. The processor then applies a neural network to the image data by calculating three-dimensional convolutions in one or more convolutional layers of the neural network and evaluating an output layer. A first dimension of the convolutions is defined in space along the spatial sequence of the two-dimensional cross-sectional images. The three-dimensional convolutions comprise convolutions along the first dimension. The output layer is connected to the one or more convolutional layers in the neural network, and has an output value that is indicative of a probability of detecting prostate cancer in the computed tomography scan. Three-dimensional convolutions in the neural network provide a more accurate probability of detecting prostate cancer.

20 Claims, 5 Drawing Sheets

(56) References Cited

OTHER PUBLICATIONS

Hao, Ruqian, et al., "A Comprehensive Study of Data Augmentation Strategies for Prostate Cancer Detection in Diffusion-Weighted MRI Using Convolutional Neural Networks", Journal of Digital Imaging (2021) 34:862-876 // https://doi.org/10.1007/s10278-021-00478-7, (Jul. 12, 2021), 862-876.

Huang, Guan, et al., "Diagnostic Value of CT in Detecting Peripheral Zone Prostate Cancer", Am. J. Roentgenol. 213, 831-835 (2019), (Oct. 2019), 831-835.

Jia, Jemianne Bautista, et al., "Prostate cancer on computed tomography: A direct comparison with multi-parametric magnetic resonance imaging and tissue pathology", European Journal of Radiology 85 (2016) 261-267, (2016), 261-267.

Kiraly, Atilla P., et al., "Deep Convolutional Encoder-Decoders for Prostate Cancer Detection and Classification", In International Conference on Medical Image Computing and Computer-Assisted Intervention, 489-497 (Springer, 2017), (2017), 489-497.

Litjens, Geert, et al., "A Survey on Deep Learning in Medical Image Analysis", Med. Image Anal. 42, 60-88 (2017), (2017), 34 pgs.

Liu, Saifeng, et al., "Prostate Cancer Diagnosis using Deep Learning with 3D Multiparametric MRI", In Medical imaging 2017: computer-aided diagnosis, vol. 10134, 1013428 (International Society for Optics and Photonics, 2017), (2017), 4 pgs.

Schelb, Patrick, et al., "Classification of Cancer at Prostate MRI: Deep Learning versus Clinical PI-RADS Assessment", Radiology 2019; 293:607-617//doi.org/10.1148/radiol.2019190938, (Dec. 2019), 607-617.

Song, Yang, et al., "Computer-Aided Diagnosis of Prostate Cancer Using a Deep Convolutional Neural Network From Multiparametric MRI", J. Magn. Reson. Imaging 2018;48:1570-1577, (Mar. 23, 2018), 1570-1577.

Wang, Xinggang, et al., "Searching for prostate cancer by fully automated magnetic resonance imaging classification: deep learning versus non-deep learning", Sci. Rep. 7, 1-8 (2017) | DOI:10.1038/s41598-017-15720-y, (Nov. 13, 2017), 8 pgs.

Yoo, Sunghwan, et al., "Prostate Cancer Detection using Deep Convolutional Neural Networks", Sci. Rep. 9, 19518. https://doi.org/10.1038/s41598-019-55972-4 (2019), (2019), 10 pgs.

Yoon, Choongheon, et al., "Automated prostate lesion detection and PI-RADS assessment with deep learning", Journal of Clinical Oncology, vol. 37, Issue 15 suppl; DOI:10.1200/JCO.2019.37.15_suppl.e16605, (May 26, 2019), 4 pgs.

\* cited by examiner

Original slice of a CT scan.

Fig. 9A

Corrupted CT scan slice.

DETECTION OF PROSTATE CANCER

CROSS-REFERENCE TO RELATED APPLICATION

The present application claims priority from Australian Patent Application No 2022202380 filed on 11 Apr. 2022, the contents of which are incorporated herein by reference in their entirety.

TECHNICAL FIELD

This disclosure relates to detecting prostate cancer from computed tomography (CT) scans.

BACKGROUND

Prostate cancer (PCa) is the second most frequent type of cancer found in men worldwide, with around one in nine men being diagnosed with PCa within their lifetime. Prostate cancer often shows no symptoms in its early stages and its diagnosis techniques are either invasive, resource intensive, or has low efficacy, making widespread early detection onerous.

As current diagnosis methods are insufficient for incidental scanning and screening programs, exploring additional modalities could lead to the discovery of an effective tool for screening and early diagnosis for PCa.

Magnetic resonance imaging (MRI) can be used as a diagnostic tool for detection of PCa. However early diagnosis for PCa from MRI scans is difficult for expertly-trained radiologists. Further, MRI scans tend to be expensive and only utilised when other diagnostic tools are exhausted.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

A method for detecting prostate cancer comprises:
receiving image data indicative of a computed tomography scan comprising a spatial sequence of two-dimensional cross-sectional images; and
applying a neural network to the image data by:
calculating three-dimensional convolutions in one or more convolutional layers of the neural network, wherein a first dimension of the convolutions is defined in space along the spatial sequence of the two-dimensional cross-sectional images and the three-dimensional convolutions comprise convolutions along the first dimension, and
evaluating an output layer, connected to the one or more convolutional layers in the neural network, the output layer having an output value that is indicative of a probability of detecting prostate cancer in the computed tomography scan.

It is an advantage that three-dimensional convolutions in the neural network provide a more accurate probability of detecting prostate cancer. This is so because the two-dimensional cross-sectional images represent cross-sections of a three-dimensional patient. Computed tomography scans are also generated for medical reasons unrelated to prostate cancer and are difficult to be used for prostate cancer diagnosis by clinicians. Therefore, it is a further advantage to detect prostate cancer in a computer tomography scan using a neural network scan as the scan is widely available and the neural network aids in diagnosis.

In some embodiments, the two-dimensional cross-sectional images represent a scan volume comprising a plurality of voxels, each of the plurality of voxels has a voxel value.

In some embodiments, the neural network comprises an input layer and each node of the input layer is associated with one of the plurality of voxels.

In some embodiments, output voxel values of each of the one or more convolutional layers comprises a weighted sum of input voxel values.

In some embodiments, the method further comprises truncating each voxel value of the plurality of voxels to lie within a value range to enhance contrast to softer tissue.

In some embodiments, each voxel value of the plurality of voxels corresponds to a Hounsfield value.

In some embodiments, the method further comprises training the neural network by applying a smoothing function to the output value of the output layer to calculate a cost value that is to be minimised during training.

In some embodiments, the method further comprises training the neural network using patient training data, the patient training data comprising computed tomography scans of clinically significant prostate cancer and control scans.

In some embodiments, training the neural network comprises pre-training the convolutional layers.

In some embodiments, pre-training the convolutional layers comprises distorting the patient training data to generate additional training data and using the distorted data to train the convolutional layers.

In some embodiments, the method further comprises reconstructing the patient training data from the distorted patient training data to train the convolutional layers.

In some embodiments, distorting the patient training data comprises, for each item of patient training data, randomly selecting two groups of voxels in the item of patient training data and swapping the voxel values.

In some embodiments, the method further comprises cropping the spatial sequence of two-dimensional cross-sectional images to include a prostate.

In some embodiments, the neural network comprises a Global Average Pooling layer.

In some embodiments, the one or more convolutional layers comprises three convolutional layers.

In some embodiments, each of the one or more convolutional layer comprises a number of convolution filters each of the size 3×3×3.

In some embodiments, the number of convolution filters in the one or more convolutional layers increases with each successive convolutional layer.

In some embodiments, the output layer is a fully connected layer.

Software, when executed by a computer, causes the computer to perform the above method.

A system for detecting prostate cancer comprises a processor configured to:

receive image data indicative of a computed tomography scan comprising a spatial sequence of two-dimensional cross-sectional images; and apply a neural network to the image data by:
calculating three-dimensional convolutions in one or more convolutional layers of the neural network, wherein a first dimension of the convolutions is defined in space along the spatial sequence of the two-dimensional cross-sectional images and the three-dimensional convolutions comprise convolutions along the first dimension, and evaluating an output layer, connected to the one or more convolutional layers in the neural network, the output layer having an output value that is indicative of a probability of detecting prostate cancer in the computed tomography scan.

Optional features provided in relation to the method, equally apply as optional features to the software and the system.

BRIEF DESCRIPTION OF DRAWINGS

An example will now be provided with reference to the following drawings.

DESCRIPTION OF EMBODIMENTS

Prostate cancer (PCa) is the second most frequent type of cancer found in men worldwide and the fifth leading cause of death by cancer. In 2018, there were 1,276,106 new cases and 358,989 deaths due to PCa. If detected in its early stages, the survival rates of PCa are high due to slow progression of the disease. Thus, with early detection and effective monitoring the odds of a patients' survival may be improved.

There are a variety of clinically approved diagnostic methods for PCa including: prostate-specific antigen (PSA) tests, digital rectal examination, transrectal ultrasounds (TRUS), PSMA-PET scans, and magnetic resonance imaging (MRI). It has been identified that PSA determination in combination with transrectal ultrasound guided biopsy often leads to false-positive results and over-treatment. The introduction of the Prostate Imaging Reporting and Data System (PI-RADS) in 2012 has led to a more standardized acquisition, interpretation, and reporting of prostate MRI. Due to this, multi-parametric MRI which relies heavily on diffusion-weighted imaging (DWI) is increasingly becoming the standard of care for PCa diagnosis.

PCa generally does not present any symptoms until it becomes locally advanced or metastatic and thus can remain asymptomatic for many years. This makes early diagnosis challenging. Historically, screening efforts have been focused on discovering these asymptomatic patients through PSA screening programs. However, the extent of both benefits and harm of screening is under continuous debate as the risk of over diagnosis is substantial. Given this and the resource intensive nature of other diagnosis methods (biopsy and MRI), several countries, including Australia, do not run any prostate cancer screening programs.

Computed tomography (CT) imaging may be a viable alternative to detecting PCa, given that the hardware and operational costs are relatively low. On top of this, patients will often have CT scans for reasons unrelated to PCa, so a CT scan of a patient is often available. However, detecting PCa in CT imaging tends to be difficult. Training humans to find evidence of it consistently may also be time consuming and expensive. By utilizing artificial intelligence (AI), along with a large sample size of PCa cases, it is possible to show whether PCa can be detected in CT scans or not and whether it can be used in a pipeline for incidental detection. Fortunately, substantial improvements in AI systems allow these systems to be used in assisting practitioners in medical image analysis tasks.

CT scanning machines use a rotating X-ray tube and a row of detectors placed in a gantry of the machine to measure X-ray attenuations by different tissues inside the body. X-ray attenuations refers to when X-ray photons, with wavelengths ranging from 10 picometers to 10 nanometers, are absorbed by the tissue when the X-ray photons pass through the body of a patient. A patient lies on a motorised table that moves horizontally, in increments, through the rotating X-ray tube and captures multiple X-ray measurements from different angles at each increment. The multiple X-ray measurements are then processed on a computer using reconstruction algorithms to produce tomographic two-dimensional cross-sectional images (virtual "slices") of a body. Each two-dimensional cross-sectional image corresponds to a different region of the patient's body as they move horizontally, in increments, through the rotating X-ray tube. The collection of two-dimensional cross-sectional images provides a three-dimensional representation of a patient's internals, which aids physicians in diagnosing internal diseases and conditions.

The two-dimensional cross-sectional (X-ray) image consists of black and white regions, as well as shades of grey. These regions correspond to the areas of the body that have attenuated the X-rays. For example, structures such as bones readily absorb X-rays and, thus, produce high contrast on the X-ray detector. As a result, bony structures appear whiter than other tissues in the X-ray image. Conversely, X-rays travel more easily through less radiologically dense tissues such as fat and muscle, as well as through air-filled cavities such as the lungs. These structures are displayed in shades of grey in the X-ray image. Regions where little to no attenuation has occurred will show up as black regions in the X-ray image.

Here, a method for applying deep convolutional neural networks (CNNs) for incidental detection of clinically significant prostate cancer (csPCa) is disclosed. The disclosed method is directed towards asymptomatic patients who had a CT scan of the abdomen/pelvis for another reason, unrelated to PCa. CNNs are able to leverage subtle cues in CTs that are not visible to humans in order to boost csPCa classification performance. The disclosed method incorporates a CNN based pipeline for csPCa classification and is trained end-to-end using patient level annotations. A key challenge in training deep CNN models for medical image analysis is the limited availability of data. To overcome this issue, the disclosed method uses a combination of self-supervised feature learning techniques and data augmentation. The performance of the disclosed method is evaluated on a dataset with 571 CT scans of the abdomen and pelvic region using cross-validation techniques and compared to the performance of expert radiologists on the same task.

The incidental screening tool of the disclosed method would aid in the detection of PCa that is in its long asymptomatic phase. This pipeline operates on all "at-risk" patients who undergo a CT scan, the pipeline may then signal an operator to perform further testing on patients with a high probability of having some form of PCa. These further tests would remain unchanged from current diagnosis methods.

While this disclosure is directed towards detecting PCa in CT scans, it is possible to use the disclosed method for the occult cancers. Occult cancers that can be incidentally detected by the disclosed method include, but are not limited to, breast, liver and soft tissue cancer. The disclosed method can be used for other three-dimensional imaging formats for the incidental detection of cancer, including, but not limited to, MRIs.

Figure 1:
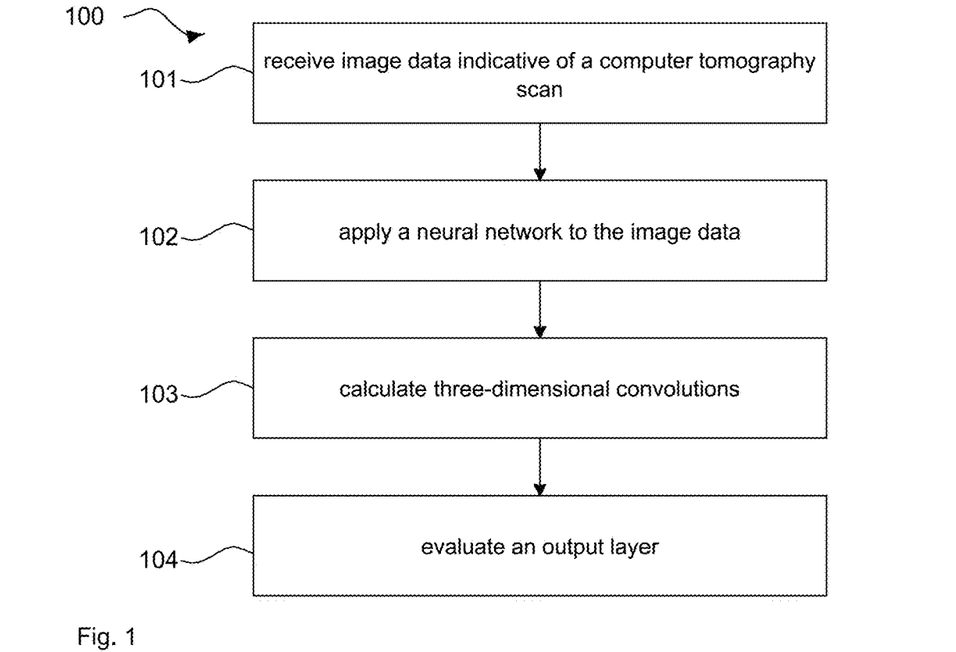
FIG. 1 illustrates a method for detecting prostate cancer.

FIG. 1 illustrates a method 100 for detecting prostate cancer. A processor performs method 100 by firstly, receiving 101 image data indicative of a CT scan. The image data indicative of a CT scan is typically a CT scan of a patient that has had the scan for reasons unrelated to PCa. The image data indicative of a CT scan also comprises a spatial sequence of two-dimensional (2D) cross-sectional images. When a patient is scanned using a CT scanning machine, the machine may capture two-dimensional cross-sectional images (or slices) of the patient incrementally. Each of the two-dimensional cross-sectional images are indicative of an X-ray image, which correspond to a different region of the patient's body as they move horizontally, in increments, through the CT scanning machine. The collection of slices gives a three-dimensional (3D) representation of the patient.

Figure 2:
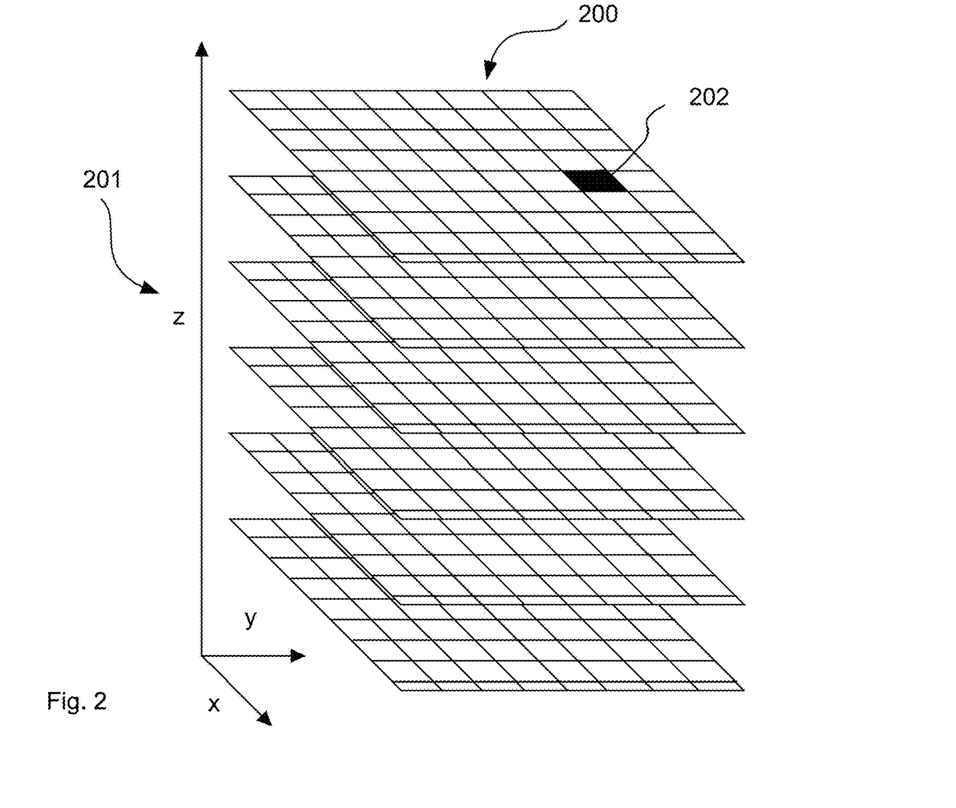
FIG. 2 illustrate an example of a spatial-sequence of two-dimensional cross-sectional images indicative of a CT scan.

FIG. 2 illustrate an example of a spatial-sequence 200 of two-dimensional cross-sectional images. The spatial sequence 200 also comprises a spatial dimension 201 and a pixel value 202 of one of the two-dimensional cross-sectional images. In FIG. 2, the spatial dimension 201 is indicative of the overall spatial sequence 200 of two-dimensional cross-sectional images. Here, the spatial dimension 201 is represented by the spatial variable z. The remaining two-dimensions are represented by the spatial variables x and y. The pixel value 202 is indicative of a Hounsfield value in a slice of a CT scan. The spatial sequence 200 of the two-dimensional cross-sectional images represent a scan volume comprising a plurality of voxels, each of the plurality of voxels has a voxel value. The voxel values are based on the pixel values from the two-dimensional cross-sectional images in the spatial sequence. In this sense, a voxel can be considered as a 3D pixel and the voxel value is based on a pixel value. In one example, a voxel is defined by the overlapping pixel between two adjacent cross-sectional images and the corresponding voxel value is based on one of the values of the overlapping pixels. In another example, the voxel value is based on both pixel values of the overlapping pixels, such as an average of the two pixel values. In a further example, a voxel is defined by the overlapping pixel between three or more adjust cross-sectional images and the corresponding voxel value is based on anyone of one the values of the overlapping pixels, such as an average of the pixel values. In this way, each voxel value of the plurality of voxels corresponds to a Hounsfield value.

The processor then applies 102 a neural network to the image data. The neural network may comprise an input layer and each node of the input layer is associated with one of the plurality of voxels. As the image data comprises a spatial sequence of two-dimensional cross-sectional images, the image data is indicative of a 3D image. As such, the processor applies 102 a 3D neural network to the image data. More specifically, the processor applies 102 a 3D neural network to the image data by calculating 103 three-dimensional convolutions in one or more convolutional layers of the neural network. In this sense, the neural network is a 3D CNN, that is trained on patient training data which comprises CT scans of csPCa and CT scan without indicators of PCa (control scans).

In calculating 103 three-dimensional convolutions, a first dimension of the convolutions is defined in space along the spatial sequence of the two-dimensional cross-sectional images. The first dimension corresponds to the spatial dimension 201 of FIG. 2. The remaining two dimensions correspond to the horizontal and vertical direction of a two-dimensional cross-sectional image. These dimensions also correspond to the x and y spatial dimensions as shown in FIG. 2. Further, calculating 103 three-dimensional convolutions comprise three-dimensional convolutions along the first dimension. In this sense, a convolutional kernel used within the convolutional layers of the neural network moves in three dimensions. In some CNNs, the convolutional kernel only moves in two dimensions, usually in the x and y direction. As such, CNNs where the convolutional kernel only moves in two dimensions is not considered to be a 3D CNN.

Figure 7:
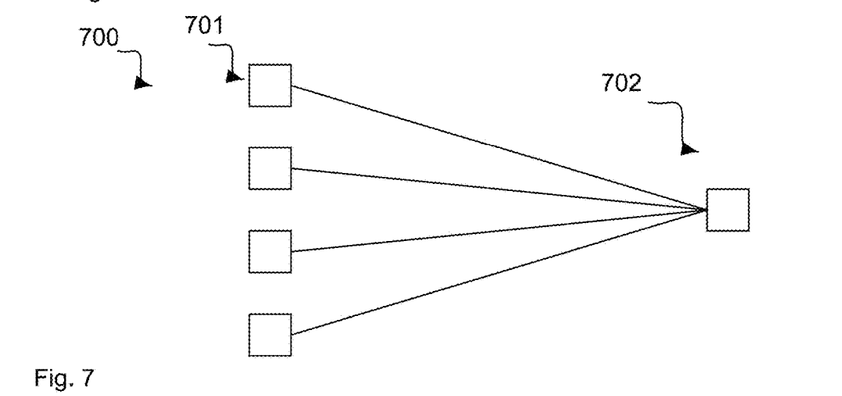
FIG. 7 illustrates a fully connected output layer with an output value corresponding to the probability of detecting prostate cancer in a CT scan.

Finally, the processor evaluates 104 an output layer. The output layer has an output value is indicative of a probability of detecting prostate cancer in the CT scan. For example, if the output value of the output layer is close to 1, then the method 100 detects a high probability of the image data containing PCa. Conversely, if the output value of the output layer is close to 0, then the method 100 detects a low probability of PCa in the image data. The output layer is a fully connected layer that is connected to the one or more convolutional layers in the neural network. FIG. 7 illustrates a fully connected output layer with an output value corresponding to the probability of detecting prostate cancer in a CT scan, which is discussed later in this disclosure.

Figure 3:
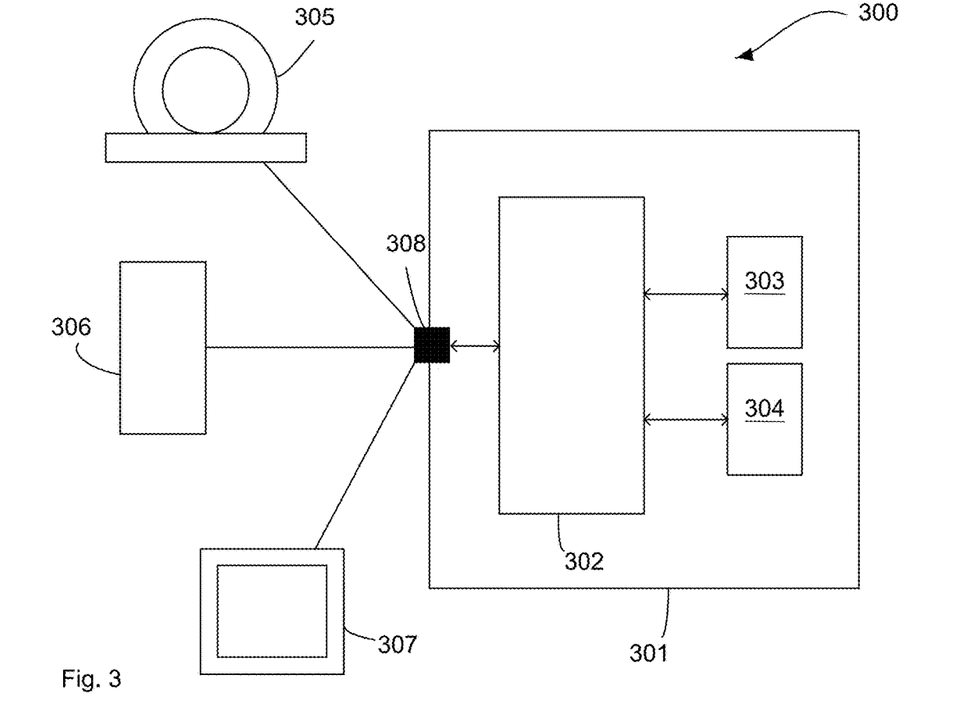
FIG. 3 illustrates a system for detecting prostate cancer.

FIG. 3 illustrates a system 300 for detecting prostate cancer. The system 300 comprises a computer 301 which itself comprises a processor 302 connected to a program memory 303 and a data memory 304. The program memory 303 is a non-transitory computer readable medium, such as a hard drive, a solid state disk or CD-ROM. Software, that is, an executable program stored on program memory 303 causes the processor 302 to perform the method in FIG. 1, that is, processor 302 receives image data indicative of a CT scan, applies a neural network to the image data, calculates three-dimensional convolutions and evaluates an output layer to predict prostate cancer in the image data. Processor 302 may then store the probability of PCa on data memory 303, such as on RAM or a processor register.

The data memory 303 may store image data indicative of a CT scan as a single-file DICOM (Digital Imaging and Communications in Medicine) or multi-file DICOM format. The data memory 303 may also store the trained neural network (the CNN) in the form of network parameters that have been optimised for calculating the output value indicative of a probability of detecting PCa. In one example, the processor 302 performs the training and stores the learned parameters of the neural network on data memory 303. Processor 302 retrieves the neural network of data memory 303 and applies the neural network to image data, thereby determining a probability of detecting PCa in the image data.

FIG. 1 is to be understood as a blueprint for the software program and may be implemented step-by-step, such that each step in FIG. 1 is represented by a function in a programming language, such as C++ or Java. The resulting source code is then compiled and stored as computer executable instructions on program memory 303.

It is noted that for most humans performing the method 100 manually, that is, without the help of a computer, would be practically impossible. In particular, it is practically impossible for a human for detect PCa from only a CT scan, especially for the purposes of early diagnosis of the PCa. Therefore, the use of a computer is part of the substance of the invention and allows performing the necessary calculations that would otherwise not be possible due to the large amount of data and the large number of calculations that are involved.

System 300 may also comprise a CT scanning machine 305, an internet server 306 and a monitor 307, which is in communication with the computer 301 via an input/output port 308. In an example, the CT scanning machine 305 scans a patient by incrementally capturing two-dimensional cross-sectional images of the patient. Each of the two-dimensional cross-sectional images are indicative of an X-ray image, which correspond to a different region of the patient's body as they move horizontally, in increments, through the CT scanning machine. The collection of cross-sectional images represent image data that is indicative of a CT scan and represents a 3D scan of the patient. Once CT scanning machine creates the image data of the patient, processor 302 receives the image data via the input/output port 308. Processor 302 then performs method 100 on the image data received from the CT scanning machine 305 and detects a probability of PCa in the image data. Additionally, the image received from the CT scanning machine 305 may be stored on the data memory 304 before and after method 100 is performed by processor 302.

In another example, the internet server 306 may store image data indicative of a CT scan. Additionally, image data may be communicated to the internet server 306 and the internet server may then communicate the image data to computer 301. The image data may be received from a source external to system 300, such as another system located remotely to system 300. The remote system may be located within the same facility as system 200 or may be completely remote from system 200. The image data indicative of a CT scan may be stored in the internet server 306 as a single-file DICOM or multi-file DICOM format. The internet server 306 may be in communication with the CT scanning machine 305, or may be in communication, over a communications network. Similarly, processor 302 receives the image data via the input/output port 308 and performs method 100 on the image data. After processor 302 performs method 100 on the image data, the image data and/or the probability of detecting prostate cancer in the image data may be communicated to the internet server 306. The internet server 306 may then communicate the image data or the probability to an external system or store them.

System 300 may also comprise a monitor 307, which may be configured to display the image data from the CT scanning machine 305 and from the internet server 306. In this way, processor 302 communicates the image data from the CT scanning machine 305 and from the internet server 306 to the monitor via the input/output port 308. Monitor 307 may be further configured to display the probability of PCa detected in image data after processor 302 performs method 100 of the image data. In this way, processor 302 communicates the probability of PCa to the monitor via the input/output port 308.

Software may provide a user interface that can be presented to the user on a monitor 307. The user interface is configured to accept input from the user, via a touch screen or a device attached to monitor 307 such as a keyboard or computer mouse. These device may also include a touchpad, an eternally connected touchscreen, a joystick, a button, and a dial. In an example, monitor 307 may display multiple instances of image data, in other words multiple CT scans, and the user may choose one of the multiple instances of image data for method 100 to be performed on, by processor 302. The user may choose one of the multiple instances of image data by interacting with the touch screen or inputting the selection with a keyboard or computer mouse. The user input may also be provided to the input/output port 308 by the monitor 307. Processor 302 may then perform method 100 on the selected image data and communicate the image data and/or the probability of detecting prostate cancer in the selected image data to monitor 307.

The processor 302 may receive data through all these interfaces, which includes memory access of volatile memory, such as cache or RAM, or non-volatile memory, such as an optical disk drive, hard disk drive, storage server or cloud storage. System 300 may further be implemented within a cloud computing environment, such as a managed group of interconnected servers hosting a dynamic number of virtual machines.

The processor 302 may receive data, such as image data, from data memory 304 as well as from the communications port 308. In one example, the processor 302 receives image data from the CT scanning machine 305 and internet server 306 via communications port 308, such as by using a Wi-Fi network according to IEEE 802.11. The Wi-Fi network may be a decentralised ad-hoc network, such that no dedicated management infrastructure, such as a router, is required or a centralised network with a router or access point managing the network.

Although communications port 308 is shown as single entity, it is to be understood that any kind of data port may be used to receive data, such as a network connection, a memory interface, a pin of the chip package of processor 302, or logical ports, such as IP sockets or parameters of functions stored on program memory 303 and executed by processor 302. Computer 301 may be configured with multiple input/output for each of the CT scanning machine 305, internet server 306 and monitor 307. The parameters of functions may be stored on data memory 304 and may be handled by-value or by-reference, that is, as a pointer, in the source code.

It is to be understood that any receiving step may be preceded by the processor 302 determining or computing the data that is later received. For example, the processor 302 determines a probability of PCa by performing method 100 and stores the probability in data memory 303, such as RAM or a processor register. The processor 302 then requests the data from the data memory 303, such as by providing a read signal together with a memory address. The data memory 303 provides the data as a voltage signal on a physical bit line and the processor 301 receives the image data via a memory interface.

FIG. 3 is one example of a configuration of system 300. However, system 300 is not strictly limited to this configuration and this may be one possible embodiment of system 300. In another embodiment, computer 301 may not be in direct communication with CT machine 305 or monitor 307 and may only in communication with the internet server 306.

Methodology

This section describes how the CT data was collected and processed for use within a deep learning algorithm. In addition it gives the details of the 3D convolutional neural network pipeline: its structure, and its training and evaluation processes.

Dataset

To train and validate the neural network architecture, CT scans were collected from an electronic clinical database. For incidental detection of prostate cancer the patients that will be scanned by the detection tool are male and aged 50 years or older (those at high-risk of PCa). However, training the neural network in the disclosed method is not limited to using only this data. This data serves as an example of a dataset that can be used to train and validate the neural network of the disclosed method.

Two different sets of scans were collected: one set of scans with PCa, and one as a control set of "healthy" prostate scans. The "PCa positive" scans will be of patients that have been diagnosed with clinically significant PCa (csPCa) (i.e., a Gleason Score of 3+4 or higher, or an International Society of Urological Pathology score of 2 or higher) with either a transrectal ultrasound-guided biopsy or prostatectomy at the time of the scan.

This criteria does not limit patients with csPCa by location within the prostate. Likewise, control cases are of patients that have no prior history or suspicion of PCa at the time of collection. Given the prevalence of PCa in the general population, some of the control subjects may have some level of PCa that was not diagnosed by the time of this study.

The two sets of scans are collectively referred to as patient training data. The disclosed method comprises training the neural network using the patient training data comprising CT scans of clinically significant prostate cancer and control scans. However, as previously indicated, the patient training data is not limited to the dataset used in this disclosure. Any dataset comprising CT scans of clinically significant prostate cancer and control scans may be used to train and validate the neural network of the disclosed method.

Data used to test the performance of the disclosed method was also collected using the above selection criteria. Through this, 571 scans were collected, 139 had clinically significant prostate cancer, and the remaining 432 were control cases. Due to the selection criteria, there was no reason to suspect that this sample will be systematically different from the population of incidental scans that will be taken in the future.

All scans were captured between the years of 2013 and 2020. The age range of the subjects were 50-103 and had a mean age of 71.6 (25th and 75th percentile ages were at 62 and 80, respectively). Likewise the Gleason scores of csPCa patients had a mean and standard deviation of X±Y.

The process of diagnosing and scanning a patient with possible PCa begins with preliminary CT and MRI scans, to check for signs of visible PCa. The PCa is then confirmed using ultrasound-guided biopsy or a prostatectomy depending on severity. Multiple diagnostic techniques are used to confirm the csPCA and should indicate how difficult detecting PCa from CT scans currently is, without screening tools such as the disclosed method.

For all patients, the scans were obtained with 64-MDCT scanners (either a Siemens SOMATOM or GE revolution) in 5 mm-thick axial sections using dual energy (unless the patient was larger than 320 cm). All examinations were performed with the patient performing a breath-hold and the following parameters: thin slice, 1 mm for Siemens SOMATOM and 1.25 mm for GE revolution; 100 ml of Optiray 350 injected IV at 2.5 ml/s during the venous phase (70 s delay); Exposure, 70-140 kV, 120 mAs.

The evaluations were done using five-fold cross validation. Each fold was selected to hold the same ratio of positives to controls (csPCa vs no known PCa) by splitting the positives and controls into five subsets separately, 28 positives and 86 controls per fold.

Data Pre-Processing

Before any pre-processing, the dimensions of the CT scans are roughly 512×512×300 voxels and contain the entire body's cross-section. To reduce the amount of unrelated data presented to the AI model and to provide a fixed sized input, each CT scan was cropped to the size 150×150×14 (in the coronal, sagittal, and axial axes, respectively). This size is the smallest size which captures the whole prostate. In this sense, the disclosed method comprises cropping the spatial sequence of two-dimensional cross-sectional images to include a prostate. However, in some cases where the prostate is small, there is a significant amount of data surrounding the prostate that is included in the input. Next, the voxel values were clipped to the range [−250 HU, 500 HU] to capture 95% of the variation in values within the prostate region and to give more contrast to the softer tissue. In this sense, the disclosed method comprises truncating each voxel value of the plurality of voxels to lie within a value range to enhance contrast to softer tissue. Finally the voxel values were normalized to the range (0,1) using the min-max normalization method. Here for each scan $\bar{x}$ the normalized scan, $\tilde{x}$ was computed as:

$$\tilde{x}_i = \frac{x_i - 500}{500 + 250}. \tag{1}$$

Figure 4A:
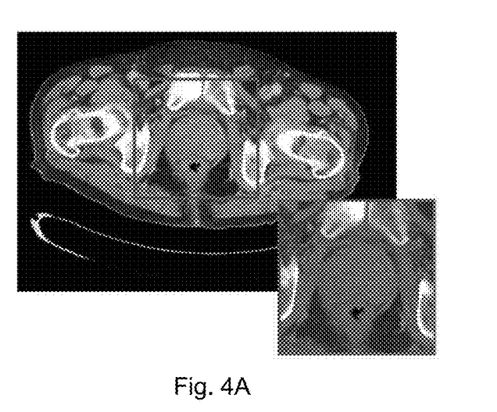
FIG. 4A illustrates a CT scan slice of a confirmed clinically significant prostate cancer patient from the dataset.
Figure 4B:
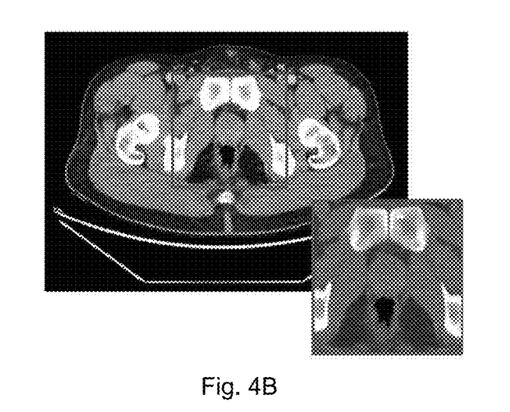
FIG. 4B illustrates a CT scan slice of a patient with no known prostate cancer (control) from the dataset.

FIG. 3 shows two CT scan slices and the corresponding pre-processed slices: one from a patient with confirmed csPCA is shown in FIG. 4A, and one from a control patient is shown in FIG. 4B.

The performance of detecting PCa by the CNN pipeline of the disclosed method is compared to radiologists on csPCA detection with CT. An in-house visualization interface is developed, which takes a CT image from the dataset and presents it to a radiologist. When presenting the information to the radiologist, two modifications were made to preprocessing which were not required for the machine learning pipeline: (1) The CT images shown to the radiologists consisted of 20 CT slices around the prostate instead of 14 (at request of the radiologists as several scans had 1 or 2 slices missing from the top of the prostate on larger than average-sized prostates). (2) The voxel normalisation was adjusted to provide more contrast for humans to see details in the prostate (range [−360 HU, 440 HU]), rather than truncating each voxel value of the plurality of voxels to lie within a value range to enhance contrast to softer tissue.

Pipeline

Processor 203 uses a deep convolution neural network to classify the CT scans into csPCa vs control. A deep CNN learns a non linear function ($f_\theta$: $\exists^{150 \times 150 \times 14} \to \{0,1\}$) that takes in a CT scan $\vec{x}$ and maps that to a value $\hat{y}_i$ in the range (0,1) depending on whether the input CT scan is from a csPCA patient ($\hat{y}_i=1$) or a control patient ($\hat{y}_i=0$).

To classify the CT scans into csPCa vs control scans, the disclosed method 100 comprises calculating 103 three-dimensional convolutions. Mathematically, a convolution is an integration function that expresses the amount of overlap of one function g as it is shifted over another function f. Intuitively, a convolution acts as a blender that mixes one function with another to give reduced data space while preserving the information. In terms of Neural Networks and Deep Learning, convolutions are filter (matrix/vectors) with learnable parameters that are used to extract low-dimensional features from an input data. They have the property to preserve the spatial or positional relationships between input data points. Convolutional neural networks exploit the spatially-local correlation by enforcing a local connectivity pattern between neurons of adjacent layers.

Figure 5:
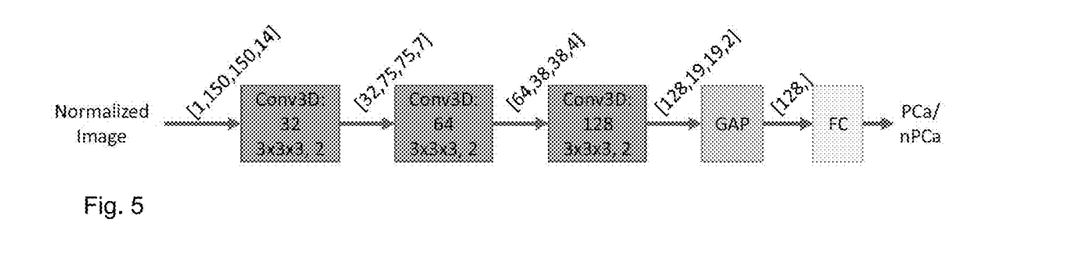
FIG. 5 illustrates the 3D convolutional neural network pipeline used for classification of CT scans.

The CNN architecture in the disclosed method consists of one or more convolutional layers. FIG. 5 shows an example structure of the CNN model used for classification and supervised training. In this example, the CNN architecture consists of three 3D-convolution layers each with convolution filters of the size 3×3×3. Each convolutional layer has convolution filters with a stride of 2 to downscale the input. The number of convolution filters in the one or more convolutional layers also increase with each successive convolutional layer.

Figure 6:
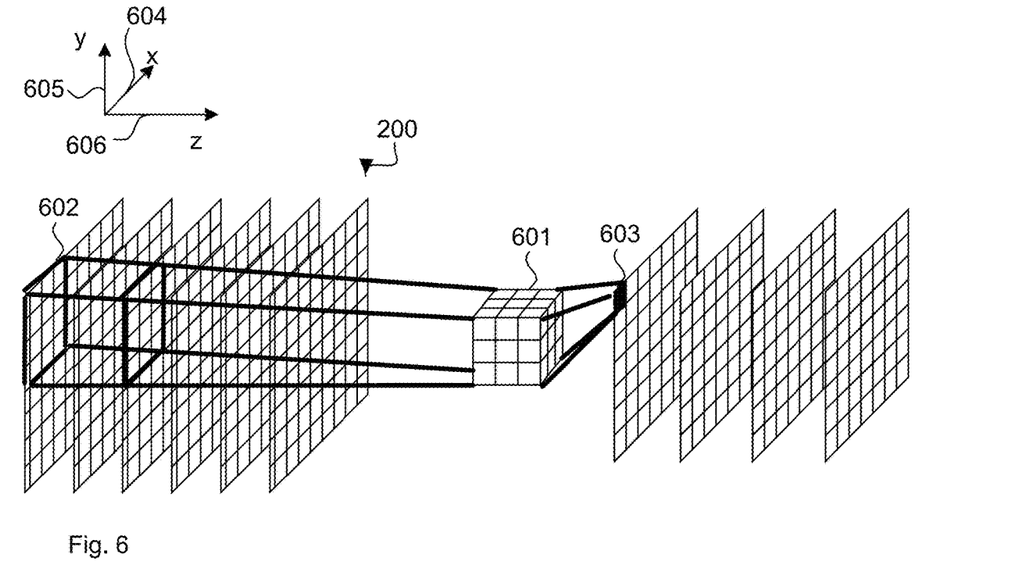
FIG. 6 illustrates a 3D convolution applied to the data structure from FIG. 2.

Here, the convolutions are applied in three dimensions and FIG. 6 illustrates a 3D convolution applied to the data structure from FIG. 3. 3D convolutions apply a 3D convolutional filter to the dataset and the filter moves in 3-directions (x, y, z) to calculate the low level feature representations. Their output shape is a 3 dimensional volume space such as cube or cuboid.

In FIG. 6 a filter 601, which is a 3×3×3 filter in this example, calculates a weighted sum of voxel values. There are 9 weights, which are the coefficients of the filter. So the filter starts at an initial position 602 in the data structure 300, multiplies each voxel value with the respective filter coefficient and adds the results. Finally, the filter 601 stores the resulting number in an output pixel 603. In this sense, the output voxel values of each of the one or more convolutional layers comprises a weighted sum of input voxel values. The weights in the weighted sum correspond to the coefficients of the filter. Then, the filter moves by one voxel along one direction in the data structure 200 and repeats the calculation for the next voxel of the output image. In the example described above, the filter will move by two voxels along one direction as the stride is 2. That direction may be an x-dimension 604 or a y-dimension 605. Importantly, the filter 601 may also move in space along the spatial sequence 606. That is, the cubic 3×3×3 filter 601 adds voxel values along the spectral dimension 606 and also moves along the spectral dimension 606. Therefore, this operation is referred to as a convolution along a dimension defined in space along the spatial sequence. It is noted that there are typically more than one filters 601, such as two or more, that create respective 3D output data structures (only one is shown in FIG. 6).

In an example, the CNN architecture comprises a batch normalization layer and ReLU activation function. As the number of convolutional filters increases with each successive convolutional layer, the number of filters in each of those convolution layers were, in the example where the stride is 2 and the convolutional filter is of the dimension 3×3×3, 32, 64, and 128. In an example, the output of the last convolution layer was then subjected to Global Average Pooling (GAP). In the example where there are three convolutional layers, this would mean that the third convolutional layer is subjected to the GAP. Finally, in an example, a fully connected layer with Sigmoid activation was used as the classifier. The Sigmoid activation represents a smoothing function used to train the CNN. However, other activation function may be used. These activation functions include, but are not limited to, a binary step function, a tanh function, a ReLU function or a softmax function. In method 100, processor 302 may evaluate 204 the output layer by applying the smoothing function to the output value of the output layer. In this sense, the activation function takes in the outputs from the hidden layers of the neural network and maps the outputs to a value between 0 and 1. Processor 302 then calculates a cost value that is to be minimised during training.

FIG. 7 illustrates an output layer 700, which is fully connected. The output layer has inputs 701 and one output 702. The inputs 701 are the results from the previous convolutional layers. That is, the convolutional layer, such as in FIG. 6 is connected to the output layer 700 to provide the results to the output layer 700. However, the convolutional layer need not be connected directly to the output layer 700 in the sense that there may be further non-convolutional layer between the convolutional layer and output layer 700. For example, there may be a max-pool layer or a GAP layer between the convolutional layer and the output layer 700.

The output layer has and output 702 and provides an output value that is indicative of a probability of detecting PCa in a CT scan. It is noted that FIG. 7 shows a simplified example of only four inputs 702, noting that in most practical applications, the number of inputs is significantly higher. Taking FIG. 6 and FIG. 7 together, this disclosure provides a deep learning network to detect prostate cancer from CT scans.

CNN Training

Given a training dataset D={($\vec{x}, y_i$)}$_{i=1}^{N}$ with N CT scans and the associated ground truth labels $y_i \in \{0,1\}$, processor 302 uses supervised learning techniques to obtain the parameters (weights) of the above CNN model. These parameters may then be stored in data memory 304. The loss function used in training the proposed CNN model was the following weighted cross entropy loss function:

$$L_{ce}(\theta) = \sum_{i=1}^{N} \left( w_i y_i \log(f_\theta(\vec{x}_i)) + w_0(1-y_i)\log(1-f_\theta(\vec{x}_i)) \right) + \lambda \|\theta\|_2^2, \quad (2)$$

However, the CNN of the disclosed method is not limited to a weighted cross entropy loss function. The CNN of the disclosed method may be trained using different loss functions. The loss function determines the cost value that is to be minimised during training. The term $w_i$, is the balancing weight for class i and used to make the loss element from each class equal, is computed as:

$$w_i = \frac{|D_i|}{|D|}, \quad (3)$$

where $|D_i|$ is the number of CT scans from class i in the training set (i=0 for the control class and i=1 for csPCA). The hyper-parameter $\lambda$ is a weight regularization coefficient (called weight decay in the AdamW optimizer used for training) that controls the complexity of the model preventing it from under/over fitting.

Training a deep CNN models from random initialization uses a large amount of data. However, as mentioned in the dataset section, only a relatively small number of data is available (for each cross validation fold, 452 CTs are used for training and 113 CTs for validation). In the disclosed method, both data augmentation and self-supervised pre-training techniques are used to create a more robust (and thus more general) model when only a small set of labelled training data is available.

In deep learning, data augmentation is a technique that transforms training inputs in a way that does not impact the classification label of the sample (rotations, translations, small amounts of noise, etc). This makes the model become more robust and generalize to samples outside of the training set distribution. For this pipeline, the input (pre-processed) CT scans are subjected to random rotations and translations during the training process. A rotation angle for each image in a given epoch was randomly selected from the set {0°,90°,180°,270°} whereas, the translations are sampled uniformly from the range [−25, 25] and [−2, 2] for height/width and depth dimensions, respectively.

In self-supervised learning, a CNN is first trained on a pretext task for which the labels can be generated through some automated process. In this sense, training the neural network comprises pre-training the convolutional layers. The knowledge gained in doing this pretext task is then used as a starting point for learning the desired (down-stream) task; in our case csPCA/control classification. The objective of self supervised learning is to leverage unlabelled data to build a feature representation that may be useful for the down-stream task.

In the disclosed method, self-supervision is used to pre-train the convolution stages of the network in FIG. 5. Patch-swap reversal was selected as the pretext task (the details of which are given below). To allow the network to perform the patch-swap reversal task, a deconvolution branch was added after the initial encoding. This can be seen in FIG. 8. This branch has the same structure as the encoder but reversed (convolution layers replaced by transpose convolutions); which reconstructs the full-sized scan from the compressed version.

Context Reconstruction (Patch Swap Reversal)

In the disclosed method, the limited amount of training data is expanded by using patch swap reversal to pre-train the convolutional layers. Pre-training the convolutional layers comprises distorting the patient training data to generate additional training data and using the distorted data to train the convolutional layers. This involves, for each item of patient training data, randomly selecting two groups of voxels in the item of patient training data and swapping the voxel values.

While the patch swap reversal method is used to create additional training data from the limited amount of data, the disclosed method is not limited to using patch swap reversal. Other self-supervised pretext tasks this can be used to train the data in the disclosed method include, but are not limited to, rotation discrimination, image in-painting, or reorder sections of an image to their correct location.

Figure 8:
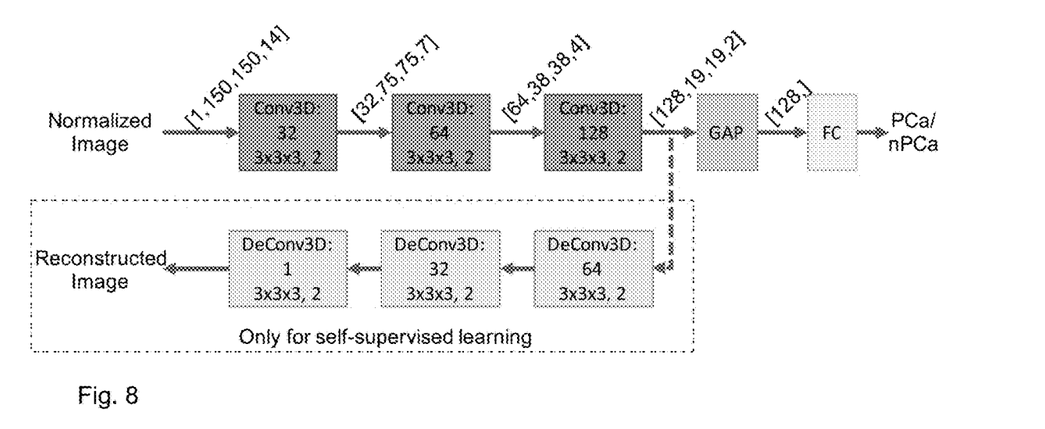
FIG. 8 illustrates the CNN pipeline with the additional reconstruction branch for the patch-swap reversal self-supervised pre-training.

FIG. 8 shows the CNN structure with the deconvolution branch used for the self-supervised pre-training. For a pretext task to yield a benefit in a downstream task, it should be able to train a network to build a strong and generalizable understanding of the dataset. One common pretext task, in-painting, uses a strong understanding of a dataset to be able to reconstruct missing data within a sample; however, as missing data is replaced with a constant value, identification of corrupt sections is too simple. A new task, patch-swap reversal, has been proposed in an attempt to rectify this issue. The main advantage and distinction in patch-swap reversal is that it maintains the same image intensity distribution throughout the corruption process as opposed to in-painting, meaning the network has a greater understanding of the dataset to identify corrupted patches before it can correct them.

Figure 9A:
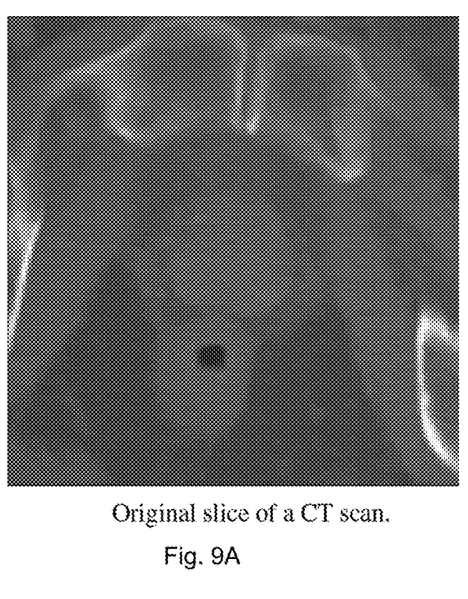
FIG. 9A illustrates an original slice of a CT scan from the patch swap reversal pretext task.
Figure 9B:
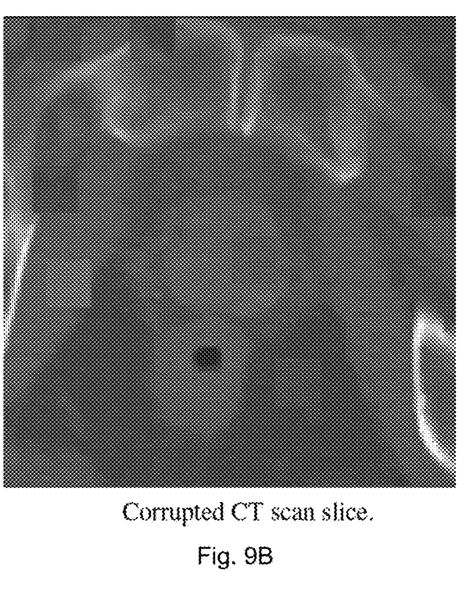
FIG. 9B illustrates a corrupted slice of a CT scan from the patch swap reversal pretext task.

An example CT scan before and after the patch swap reversal process is shown in FIGS. 9A-9B. FIG. 9A illustrates an original slice of a CT scan from the patch swap reversal pretext task, while FIG. 9B illustrates a corrupted slice of a CT scan from the patch swap reversal pretext task. In patch swap reversal, for each training image, $x_i$, a corrupted or distorted version of that image, $\hat{X}_i$, is generated by: randomly selecting two small patches in the original image and then swapping the voxel values between them. This swapping process is repeated for a predetermined number of times on each image. As an example, the patch size is set to 20×20×3 with 15 swap operations for each image (for a total of 30 patches).

Once the dataset, $\{(X_i,\hat{X}_i)\}_{i=1}^{N}$, is generated, the network is trained to reconstruct the original image $x_i$ using the corrupted version of it $\hat{X}_i$. In this sense, the disclosed method comprises reconstructing the patient training data from the distorted patient training data to train the convolutional layers. The loss function for the pretext task was the mean squared error (L2 norm) between the reconstructed image and the original image.

$$L_{12} = \frac{1}{N}\sum_{i=0}^{N}\|X_i - f_{\theta_2}(\hat{X}_i)\|_2^2. \quad (4)$$

However, the pre-training task in the disclosed method is not limited to a loss function corresponding to the mean squared error. The model was trained using the AdamW optimizer. First it trained on the pretext task with learning rate 3e-4 for 60 epochs, then trained for a further 100 epochs with a learning rate of 3e-5 on the csPCA vs control classification (down-stream) task.

Results

Here, the performance of the proposed CNN pipeline on CT is evaluated based prostate cancer classification and compared with the performance of radiologists (on the same task). Metrics used include Receiver Operating Characteristics (ROC), sensitivity, specificity and Cohen's Kappa matrices, computed via five-fold cross validation, to quantify the performance of the model in separating confirmed csPCA and control cases. All experiments were executed in PyTorch on a computer with Intel Xeon E5-1650 CPU with an NVIDIA GTX Titan X GPU, 16 GB RAM and Ubuntu 16.04 OS.

First, each element of the proposed pipeline was identified using an ablation study. Here, processor 302 trains the neural network using four different variants of our pipeline:

No data augmentation or self supervision
Only self supervision (no data augmentation)
Only data augmentation (no self supervision)
Both data augmentation and self supervision (proposed method)

TABLE 1

The results from the ablation study: the mean and 95% Confidence Interval of the area under the ROC curves measured using 5-fold cross validation.

|  | No Pre-training | Patch Swap reversal SSL |
|---|---|---|
| No Augmentation | 0.821 (95% CI: 0.79-0.86) | 0.842 (95% CI: 0.80-0.88) |
| With Augmentation | 0.845 (95% CI: 0.82-0.87) | 0.877 (95% CI: 0.86-0.90) |

The results of the ablation study is presented in Table 1. The results show that the model trained without augmentation or self supervision was only able to achieve a ROC-AUC of approximately 0.82. Adding data augmentation and self supervision independently, improved the performance of the model to around 0.845 and 0.842, respectively. The model trained with both data augmentation and self-supervision was able to achieve significantly better performance (ROC-AUC$\approx$0.877). The above results show that both data augmentation and patch-swap reversal based self-supervision can help the training process to converge to a model that generalizes well to test data.

Next, the performance of the model on classifying prostate cancer on CT scans is compared with the performance of human experts (i.e. radiologists). For this experiment, 115 CT scans were randomly selected from the original dataset (corresponds to one of the five folds used in the cross validation) that consisted of 28 scans from confirmed csPCA patients and 87 control patients. The random sampling led to minor variations in age range and Gleason score distribution; but remains representative of the total population. The mean age raised from 71.6 to 72.1.

This small change indicates that the smaller sample is representative of the overall dataset. This data subset was then presented to two expert radiologists with 7 and 10 years of experience respectively. The radiologists examined the CT scans and annotated each scan with two labels: 1) Does the scan contain indications of csPCA (or not), and 2) A confidence level (from 0 to 5) quantifying their confidence in making the decision. In order to compute the AUC values, the annotations by the radiologists were converted to probabilities using the following procedure. If the radiologist had the highest confidence level (5) and had found no prostate cancer this would be considered a score of 0; likewise, if they had found prostate cancer with high confidence it would be a score of 1. If the radiologist had zero confidence, regardless of whether prostate cancer was found or not the score would be 0.5. The values between were obtained using linear interpolation on confidence level; lower confidence means the score is closer to 0.5.

TABLE 2

Performance comparison between proposed CNN pipeline and two radiologists on PCa classification with CT scans.

|  | Proposed CNN Pipeline | Radiologist 1 | Radiologist 2 |
|---|---|---|---|
| ROC-AUC | 0.877 | 0.613 | 0.697 |
| Sensitivity | 0.556 | 0.444 | 0.741 |
| Specificity | 0.988 | 0.671 | 0.600 |

Figure 10:
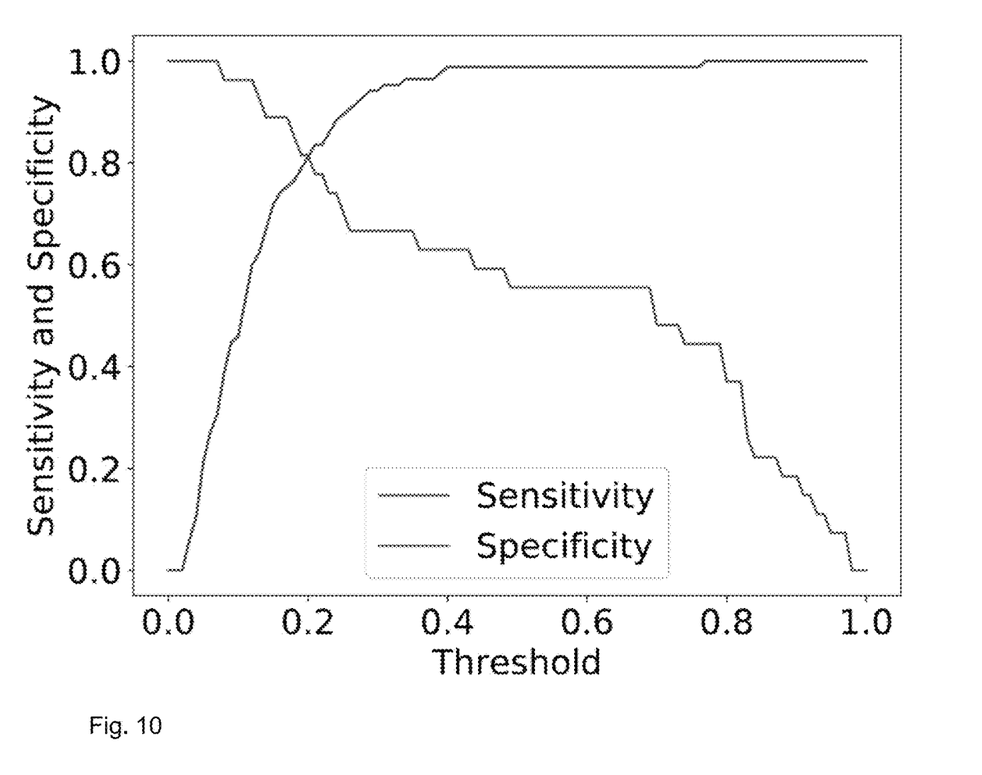
FIG. 10 illustrates the Sensitivity and Specificity Curves of the Proposed CNN Pipeline with respect to the chosen threshold.

Table 2 compares the performance of the proposed CNN model with the expert radiologists. The results show that the ROC-AUC for both radiologists are between 0.61-0.70. Radiologist 1 inclined towards achieving a high specificity while Radiologist 2 inclined towards achieving a high sensitivity. In comparison, the proposed CNN model has achieved a significantly higher ROC-AUC ($\approx$0.87) with a specificity of 0.99. When calculating the sensitivity/specificity for the proposed CNN model, a threshold of 0.5 is used which gives a high specificity but low sensitivity of 0.56. For most applications a higher sensitivity is desired, but in incidental detection applications it can be argued that a higher specificity is useful to push uncertain cases towards further testing. If a higher sensitivity is required, one can set the threshold to 0.2 which may give both a sensitivity and specificity of $\approx$0.8, the full spectrum of sensitivities and specificities for the complete dataset is shown in FIG. 10.

TABLE 3

Cohen's Kappa Agreement between the proposed CNN pipeline, radiologists, and ground truth labels.

| Proposed CNN Pipeline | 0.632 |  |  |
|---|---|---|---|
| Radiologist 1 | 0.086 | 0.107 |  |
| Radiologist 2 | 0.254 | 0.157 | 0.191 |
|  | Ground-truth Labels | Proposed CNN Pipeline | Radiologist 1 |

Table 3 shows the Cohen's Kappa Agreement between the proposed CNN model, radiologists, and the ground truth labels. Cohen's Kappa is a measure between (−1, 1) where a value of 0 indicate no agreement and a value of +1 indicate perfect agreement and −1 indicates perfect disagreement. The results show that the agreement between the proposed CNN model and ground truth labels is moderate. However, the two radiologists showed minimal to no agreement with the ground truth labels. Furthermore, the agreement between the two radiologists in csPCA scan classification is also minimal.

The above results, in line with the previous observations, show that for humans, CT scans do not provide adequate information to classify csPCA accurately. Overall, these exclusions make the task of detection of PCa in CT scans easier, and are less representative of daily clinical practice as opposed to a non-curated set of samples. However it is often difficult to identify small or early prostate cancer and therefore in daily clinical practice they would raise the possibility of prostate cancer when they identify cases with large enhancing tumours, when the tumour extends beyond the prostate or when they identify lymph node and bone metastasis.

The proposed CNN model has been able to utilize the information in CT scans to classify clinically significant PCa cases vs cases with no known PCa at a level that is deemed adequate for incidental detection of PCa.

Discussion

Figure 11:
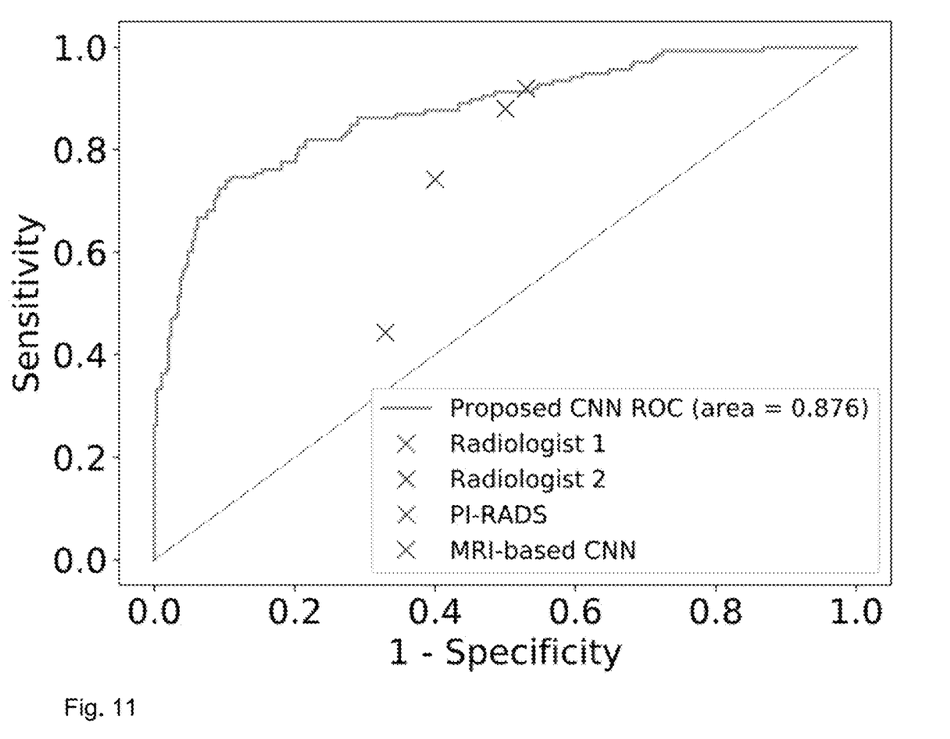
FIG. 11 illustrates the ROC Curve of the proposed CNN model in comparison to the sensitivity and specificity of the two radiologists, PI-RADS, and deep learning systems on MRIs.

FIG. 11 shows an overview of the comparison of the proposed CNN pipeline with the reported performance of MRI based prostate cancer detection with PI-RADS and deep CNN based models, and humans observing CT scans. The values for PI-RADS and the deep CNN models were obtained from prior art (MRI-based CNN). The intention here is to show that the proposed pipeline had adequate performance level to be used for incidental detection.

FIG. 11 shows that the proposed CT deep learning model performs similarly to PI-RADS and other MRI-based deep learning model at equivalent sensitivities/specificities. The small variations in the AUC values can likely be attributed to the use of strong data augmentation, self-supervised pre-training or different difficulty level of the datasets used. These results comparisons further indicate that CT scans do hold information that is useful for classifying prostate cancer.

In comparison to PSA tests (another diagnosis technique that gives a probability and no localisation information), the pipeline of the disclosed method has superior performance. According to prior records: PSA tests currently have a sensitivity of 0.32 and specificity of 0.85 when checking for total PSA is less than 3 ng/mL compared to the pipeline of the disclosed method, achieving a sensitivity and specificity of 0.56 and 0.99 respectively.

Figure 12A:
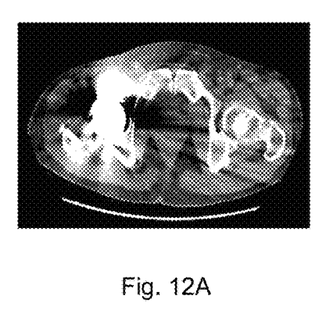
FIG. 12A illustrates an example of a CT artefact with the dataset caused by metallic implants.
Figure 12B:
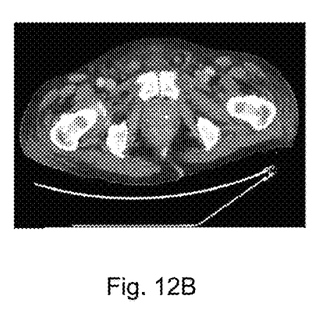
FIG. 12B illustrates an example of prostatic calculi seen in a CT scan with the dataset.
Figure 12C:
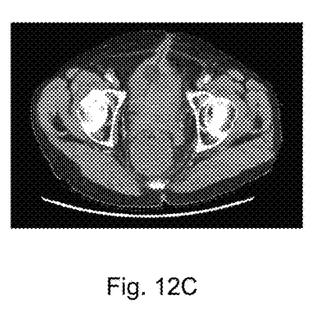
FIG. 12C illustrates an example of a CT scan with a catheter inside the bladder with the dataset.

A qualitative evaluation of the proposed CNN based pipeline in the disclosed method was also conducted. For this evaluation strong false positives, false negatives, true positives and true negatives were extracted from the model and they were showed to an expert radiologist. Many of the false positive samples had other issues within the scan that were not prostate cancer; such catheters, and prostatic calculi (as seen as a small white dot in the prostate). Some examples of this can be seen in FIG. 12A-12C. FIG. 12A illustrates an example of a CT artefact with the dataset caused by metallic implants. FIG. 12B illustrates an example of prostatic calculi seen in a CT scan with the dataset. FIG. 12C illustrates an example of a CT scan with a catheter inside the bladder with the dataset.

Likewise, some of the false negatives were of scans with insufficient contrast level. Such issues can be avoided by either including more data with anomalies in the dataset or by doing an image quality classification before the images are fed to the CNN model. However, for the strong true positives no trend was seen, giving some evidence that there is no confounding element that the CNN identifies as PCa incorrectly.

Conclusion

In this disclosure, a 3D convolutional neural network based pipeline is presented for incidental detection of prostate cancer patients using contrast enhanced CT scans. An incidental screening tool for prostate cancer has the potential to improve health outcomes as it could prompt further testing of patients who are in the long initial asymptomatic phase of the cancer. The model of the disclosed method was evaluated by performing five-fold cross validation on a dataset of 571 CT scans (139 scans from clinically significant prostate cancer patients confirmed either via transrectal ultrasound-guided biopsy or MRI and, 432 control patients with no known prostate cancer) along with a comparison to human radiologists on the same dataset and similar pipelines operating on MRIs. The proposed pipeline of the disclosed method achieved an area under the receiver operating characteristic curve (ROC-AUC) of 0.88 (95% Confidence Interval: 0.86-0.90) at patient level PCa detection on CT which was significantly better than the human performance on the same task. Likewise, the results also show that CT in combination with deep learning can perform comparably to MRI based diagnostic pipelines. Overall, these results show that CT scans do contain enough information to separate PCa scans from non-PCa scans and thus gives a strong promise for real world applications of the pipeline in incidental detection of prostate cancer using CT scans.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for detecting prostate cancer, the method comprising:
receiving image data indicative of a computed tomography scan comprising a spatial sequence of two-dimensional cross-sectional images; and
applying a trained neural network to the image data by:
calculating three-dimensional convolutions in one or more convolutional layers of the trained neural network, wherein a first dimension of the convolutions is defined in space along the spatial sequence of the two-dimensional cross-sectional images and the three-dimensional convolutions comprise convolutions along the first dimension, and
evaluating an output layer, connected to the one or more convolutional layers in the trained neural network, the output layer having an output value that is indicative of a probability of detecting prostate cancer in the computed tomography scan,
wherein:
the trained neural network is trained on patient training data,
the patient training data comprises image data with labels indicative of prostate biopsy results of the patient, and
the image data of the patient training data is indicative of a computed tomography scan incidentally obtained from the patient prior to a corresponding prostate biopsy.

2. The method of claim 1, wherein the two-dimensional cross-sectional images represent a scan volume comprising a plurality of voxels, each of the plurality of voxels has a voxel value.

3. The method of claim 2, wherein the trained neural network comprises an input layer and each node of the input layer is associated with one of the plurality of voxels.

4. The method of claim 2, wherein output voxel values of each of the one or more convolutional layers comprises a weighted sum of input voxel values.

5. The method of claim 2, further comprising truncating each voxel value of the plurality of voxels to lie within a value range to enhance contrast to softer tissue.

6. The method of claim 2, wherein each voxel value of the plurality of voxels corresponds to a Hounsfield value.

7. The method of claim 1, further comprising training a neural network to generate the trained neural network by applying a smoothing function to the output value of the output layer to calculate a cost value that is to be minimised during training.

8. The method of claim 7, further comprising training the neural network using the patient training data, the patient training data comprising computed tomography scans of clinically significant prostate cancer and control scans.

9. The method of claim 7, wherein training the neural network comprises pre-training the one or more convolutional layers.

10. The method of claim 9, wherein pre-training the one or more convolutional layers comprises distorting the patient training data to generate additional training data and using the distorted data to train the one or more convolutional layers.

11. The method of claim 10, further comprising reconstructing the patient training data from the distorted patient training data to train the one or more convolutional layers.

12. The method of claim 10, wherein distorting the patient training data comprises, for each item of patient training data, randomly selecting two groups of voxels in the item of patient training data and swapping the voxel values.

13. The method of claim 1, further comprising cropping the spatial sequence of two-dimensional cross-sectional images to include a prostate.

14. The method of claim 1, wherein the trained neural network comprises a Global Average Pooling layer.

15. The method of claim 1, wherein the one or more convolutional layers comprises three convolutional layers.

16. The method of claim 1, wherein each of the one or more convolutional layers comprises a number of convolution filters each of the size 3×3×3.

17. The method of claim 16, wherein the number of convolution filters in the one or more convolutional layers increases with each successive convolutional layer.

18. The method of claim 1, wherein the output layer is a fully connected layer.

19. A non-transitory, computer readable medium with program code stored thereon that when executed by a computer, causes the computer to perform the method of claim 1.

20. A system for detecting prostate cancer, the system comprising a processor configured to:
receive image data indicative of a computed tomography scan comprising a spatial sequence of two-dimensional cross-sectional images; and
apply a trained neural network to the image data by:
calculating three-dimensional convolutions in one or more convolutional layers of the trained neural network, wherein a first dimension of the convolutions is defined in space along the spatial sequence of the two-dimensional cross-sectional images and the three-dimensional convolutions comprise convolutions along the first dimension, and
evaluating an output layer, connected to the one or more convolutional layers in the trained neural network, the output layer having an output value that is indicative of a probability of detecting prostate cancer in the computed tomography scan,
wherein:
the trained neural network is trained on patient training data,
the patient training data comprises image data with labels indicative of prostate biopsy results of the patient, and
the image data of the patient training data is indicative of a computed tomography scan incidentally obtained from the patient prior to a corresponding prostate biopsy.

* * * * *